US008801786B2

(12) United States Patent
Bernard et al.

(10) Patent No.: US 8,801,786 B2
(45) Date of Patent: Aug. 12, 2014

(54) VERTEBRAL OSTEOSYNTHESIS MATERIAL

(75) Inventors: Pierre Bernard, Caen (FR); Vincent Fiere, Lyons (FR)

(73) Assignee: Medicrea International, Neyron (FR)

( * ) Notice: Subject to any disclaimer, the term of this patent is extended or adjusted under 35 U.S.C. 154(b) by 622 days.

(21) Appl. No.: 13/003,086

(22) PCT Filed: Jul. 22, 2009

(86) PCT No.: PCT/IB2009/053181
§ 371 (c)(1),
(2), (4) Date: Jan. 7, 2011

(87) PCT Pub. No.: WO2010/010522
PCT Pub. Date: Jan. 28, 2010

(65) Prior Publication Data
US 2011/0118842 A1      May 19, 2011

(30) Foreign Application Priority Data
Jul. 24, 2008   (FR) ...................... 08 55059

(51) Int. Cl.
*A61F 2/44*          (2006.01)
(52) U.S. Cl.
USPC .................... 623/17.11; 623/17.16
(58) Field of Classification Search
USPC ............. 606/74, 75, 313, 326, 327, 329; 623/17.11–17.16
See application file for complete search history.

(56) References Cited

U.S. PATENT DOCUMENTS

| | | | | |
|---|---|---|---|---|
| 5,601,558 A | * | 2/1997 | Torrie et al. | 606/326 |
| 5,993,476 A | * | 11/1999 | Groiso | 606/219 |
| 6,120,503 A | * | 9/2000 | Michelson | 606/86 A |
| 6,187,009 B1 | * | 2/2001 | Herzog et al. | 606/75 |
| 6,558,423 B1 | * | 5/2003 | Michelson | 623/17.11 |
| 7,344,539 B2 | * | 3/2008 | Serhan et al. | 623/13.11 |
| 2008/0167666 A1 | | 7/2008 | Fiere et al. | |

FOREIGN PATENT DOCUMENTS

FR         2 885 514 A1    11/2006
WO     WO 02/34120 A2      5/2002

OTHER PUBLICATIONS

International Search Report issued in Application No. PCT/IB2009/053181, dated Sep. 18, 2009.
Written Opinion of the International Searching Authority issued in Application No. PCT/IB2009/053181; Dated Sep. 18, 2009.

* cited by examiner

*Primary Examiner* — Nicholas Woodall
(74) *Attorney, Agent, or Firm* — Oliff PLC

(57) ABSTRACT

A graft or an intervertebral piece or cage designed to be inserted between two vertebrae, and an implant in the form of a staple, having two lateral branches designed to be inserted into the plates of the respective vertebrae to be immobilized and a central branch connecting these two lateral branches to each other. At least one lateral branch has at least one mobile portion, movable between an introduction position, in which this mobile portion is located in the extension of the rest of this lateral branch, and an anchoring position, in which this mobile portion protrudes laterally in relation to the rest of the lateral branch, and the implant has movement means allowing the mobile portion to move between the introduction and anchoring positions.

16 Claims, 3 Drawing Sheets

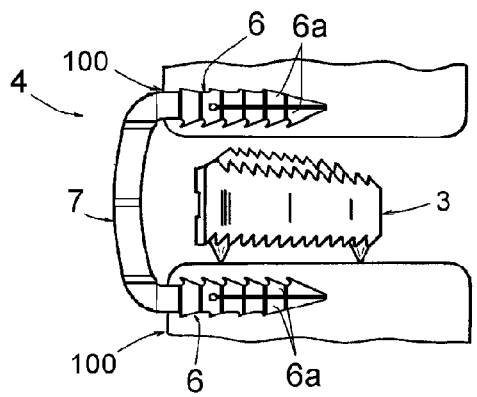
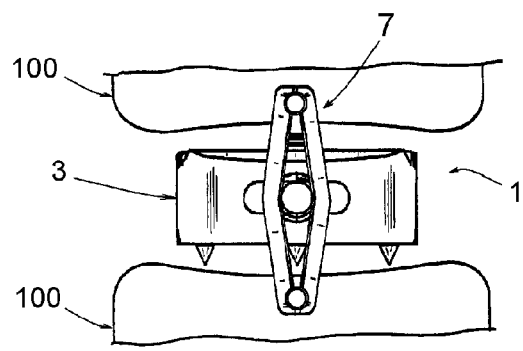
FIG. 12  FIG. 13
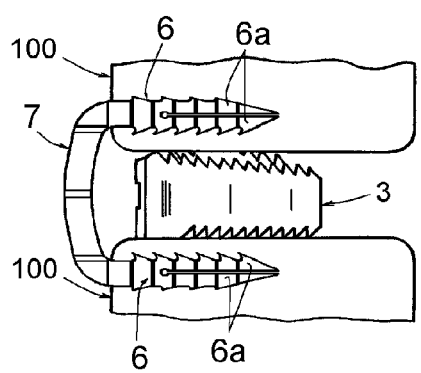
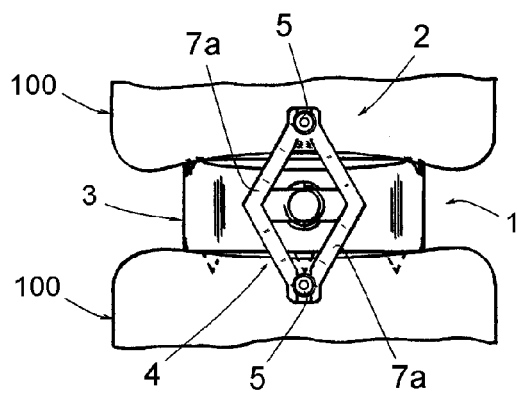
FIG. 14  FIG. 15
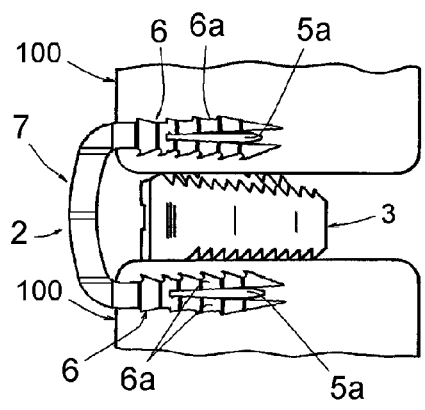
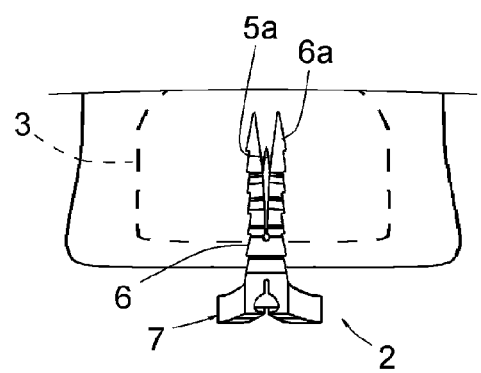
FIG. 16  FIG. 17

VERTEBRAL OSTEOSYNTHESIS MATERIAL

The present invention concerns a vertebral osteosynthesis material.

The performance of a vertebral osteosynthesis involves repositioning the vertebrae suitably in relation to each other, then completely immobilizing these vertebrae. This immobilization is obtained by inserting a bone graft or intervertebral implant between the two vertebrae and immobilizing these vertebrae using an osteosynthesis implant for the time needed for a growth of bone cells to occur.

One known vertebral osteosynthesis implant is described by French patent application no. 05 04745, in the applicant's name. This implant is in the form o a staple comprising two lateral branches designed to be inserted into the plates of the respective vertebrae to be immobilized, and a central branch with two bent portions giving it a diamond shape. This central branch can be shortened by transverse deformation of said bent portions, so as to bring the lateral branches closer to each other and therefore to bring the two vertebrae closer together so as to apply them tightly against a graft or an intervertebral piece or cage inserted between these vertebrae.

This implant is of great practical interest in relation to other existing techniques for maintaining vertebrae using plates held by screws, but does, however, present a notable risk of the appearance of play of the vertebrae in relation to it, or even of expulsion of the plate outside the vertebral bodies. This expulsion, if it occurs, requires a new surgical procedure in order to eliminate any risk of damaging nearby tissue.

The result is that the practical interest of the implant is substantially offset by this risk of the appearance of play or of expulsion.

The present invention aims to resolve this essential drawback.

The vertebral osteosynthesis material which it concerns comprises, in a known manner, a graft or an intervertebral piece or cage designed to be inserted between two vertebrae, and an implant in the form of a staple, having two lateral branches designed to be inserted into the plates of the respective vertebrae to be immobilized and a central branch connecting these two lateral branches to each other by forming a single piece with them; each lateral branch has a longitudinal central axis; the central branch can be shortened after implantation so as to allow said lateral branches to come closer to each other and to thus achieve tight application of the vertebrae on the graft or on the intervertebral piece or cage.

According to the invention,
- at least one lateral branch comprises at least one mobile portion, movable between an introduction position, in which this mobile portion is located close to said longitudinal central axis of the lateral branch and in the extension of the rest of this lateral branch, and an anchoring position, in which this mobile portion is moved away from said longitudinal central axis of the lateral branch and protrudes laterally in relation to the rest of the lateral branch, the lateral branch thus having, in this anchoring position, at said mobile portion, a transverse section greater than that of the hole having allowed the introduction of this branch into the vertebral body of the vertebra receiving said lateral branch;
- each mobile portion is provided with protruding reliefs able to be inserted into the bone of a vertebra, and
- the implant comprises movement means, allowing the movement of said mobile portion between said introduction and anchoring positions.

The implant according to the invention can thus be placed in the same way as the known implant, by simultaneous introduction of its two lateral branches into holes arranged in the vertebral bodies of the respective vertebrae, the mobile portion(s) of one lateral branch or of both lateral branches then being in the introduction position. Once the lateral branches are implanted in the vertebral bodies, said movement means are actuated so as to bring said mobile portion(s) into the anchoring position, thereby ensuring resistant anchoring of the implant to the vertebral bodies.

The inventors have indeed been able to observe that the risk of the appearance of play of the vertebrae in relation to the implant, or even of expulsion of the implant, was the result of a tendency of the two treated vertebrae to come closer to each other over time, following a more or less pronounced insertion of the graft or of the intervertebral piece or cage in one and/or the other of the vertebrae, or following compression of the graft. This approaching leads, with the existing implant, to a loss of pressure of the teeth of the lateral branches with regard to the vertebral bodies of the vertebrae and therefore to a strong reduction of the maintenance of the implant in the vertebrae along the longitudinal direction of these lateral branches.

On the contrary, the implant according to the invention makes it possible, thanks to the assuming by said mobile portion of the anchoring position after implantation, to achieve anchoring of the implant which is not dependent on the position of the vertebrae in relation to each other, and therefore to ensure complete maintenance of the implant in the implantation position whether or not the vertebrae are close to each other.

This complete anchoring is furthermore effective notwithstanding the reduced dimensions of the contact surfaces between the implant and the bone tissues, the repeated stresses exerted by the vertebrae on the implant and the quality of the bone of the vertebrae, which vary from one patient to the next.

According to one simple embodiment of the invention,
- said lateral branch comprises at least one slot which goes all the way through it and an internal channel extending from the zone of this lateral branch connected to said central branch to the portions of this lateral branch defined by said slot(s), and
- said movement means comprise a rod designed to be engaged in said internal channel up to between said portions of the lateral branch defined by said slot(s), so as to separate these portions from each other.

Said portions defined by said slot constitute mobile portions as previously mentioned; said introduction position corresponds to a non-separated position of these portions whereas the anchoring position corresponds to the mutually separated position of these portions.

Said slot(s) can be arranged from the free end of the lateral branch, such that they lead into this end.

Alternatively, said slot(s) are arranged such that they do not open into the free end of the lateral branch.

Said lateral branch can only comprise a single slot. This slot is, in this case, preferably arranged in the plane in which the two lateral branches of the implant extend, such that the mobile portions defined by said slot are mobile in a plane perpendicular to that in which the two lateral branches of the implant extend. In other words, said mobile portions separate from each other in directions perpendicular to the direction in which the two lateral branches come closer to each other.

Said slot can, however, also be arranged in a plane perpendicular to the plane in which the two lateral branches of the implant extend, such that said mobile portions defined by this slot move away from each other in directions parallel to the direction in which these two lateral branches come closer to each other.

Said lateral branch can also comprise several slots, and in particular two perpendicular slots defining four mobile portions of the branch able to move away from each other in the anchoring position.

Preferably, at least one slot, on the proximal side, opens into a bore arranged in said lateral branch transversely to said longitudinal central axis.

This bore favors the deformation of the material of said branch, which allows the separation of said mobile portions defined by the slot, and makes it possible to distribute, over an extended surface, the stress exerted on this material by this separation, thereby avoiding any beginning of cracking of this material.

Said rod constituting the movement means can simply be smooth and dimensioned such that it is engaged forcibly inside said internal channel. It can also comprise a screw thread whereas this internal channel comprises a corresponding tapping, this screw thread and this tapping enabling engagement of this rod in this channel by screwing.

In the first case, the material constituting said lateral branch is advantageously a material having a degree of elastic deformability. The rod is held in the lateral branch simply due to the tightening exerted on it by said portions defined by said slot(s), by elastic return.

Advantageously, said internal channel has a slender shape at said portions defined by said slot(s), and said rod has a slender distal end.

These slender shapes allow progressive separation of said portions defined by said slot(s) as the rod is introduced into the internal channel. They therefore allow a progressive increase of the stress to be exerted on said rod in order to introduce this rod inside this channel and realize the separation of the portions defined by said slot(s), facilitating the placement of this rod.

Advantageously,
  said rod has a body and a proximal head with a diameter greater than that of the body, such that a shoulder is defined between this head and this body, and
  said internal channel has a distal portion and a proximal portion with a diameter greater than the diameter of the distal portion, such that a shoulder is defined between these proximal and distal portions,
these respective shoulders making it possible, through their abutment, to define a position of complete introduction of said rod into said lateral branch.

This position of complete introduction therefore makes it possible to define a precise position of complete engagement of the rod in said internal channel.

According to other possible embodiments of the invention, said mobile portions could be made up of deployable portions, such as tongues.

Preferably, each of the two lateral branches of the implant comprises at least one mobile portion as previously mentioned and movement means as previously mentioned.

The two lateral branches thus allow reinforced anchoring in the plate of the corresponding vertebra.

Preferably, said lateral branch comprising said at least one mobile portion has a square or rectangular transverse section, such that it has four flat lateral faces, each of these four flat lateral faces having protruding reliefs able to be inserted into the bone of a vertebra.

These protruding reliefs can in particular be one or several series of teeth or steps.

The surgical method using the material according to the invention comprises the following steps:
  in any order, insertion of a graft or an intervertebral piece or cage between two vertebrae and arrangement in the plates of these vertebrae of holes for receiving lateral branches of the implant;
  engagement of the lateral branches of the implant in these receiving holes, said at least one mobile portion being in the introduction position;
  shortening of said central branch so as to make it possible to bring said lateral branches closer to each other and thereby achieve a tight application of the vertebrae on the graft or the intervertebral piece or cage;
  movement of said at least one mobile portion into the anchoring position.

This method can also comprise a subsequent step of connecting the central branch to said intervertebral piece or cage.

The invention will be well understood, and other characteristics and advantages thereof will appear, in reference to the appended diagrammatic drawing, illustrating, as non-limiting examples, several possible embodiments of an implant comprised by the vertebral osteosynthesis material it concerns.

FIGS. 12 and 13 are sagittal and anteroposterior views, respectively, of the material including a piece in staple form according to FIGS. 8 and 9, during placement on two vertebrae and before bringing these vertebrae closer together;

FIGS. 14 and 15 are views similar to FIGS. 12 and 13, respectively, after bringing the vertebrae closer together;

FIG. 16 is a view of the material similar to FIG. 14, in a final implantation position, and FIG. 17 is a view of the material along the apico-caudal axis, in said final implantation position.

Figure 1:
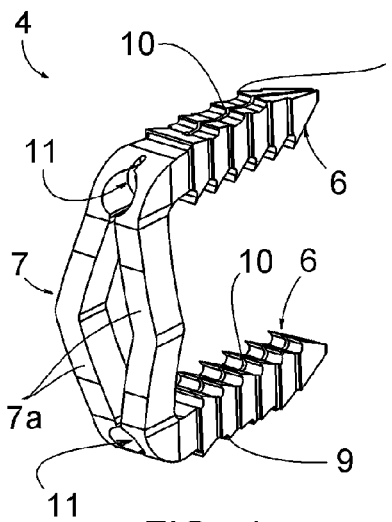
FIG. 1 is a perspective view of a piece in staple form comprised by this implant, according to a first embodiment.
Figure 2:
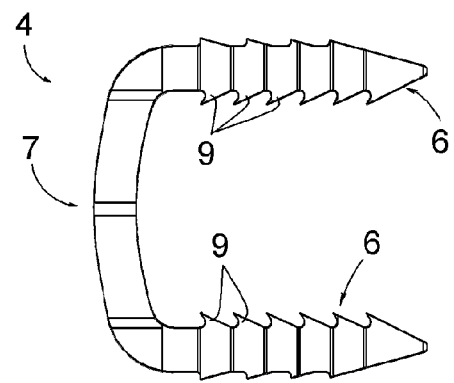
FIG. 2 is a side view of this piece.
Figure 3:
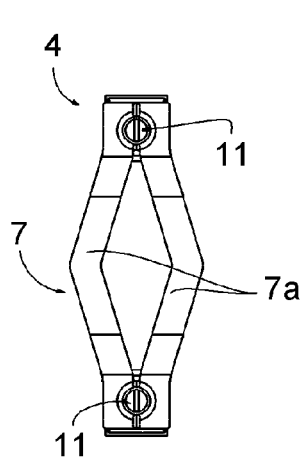
FIG. 3 is a profile view of this piece, by its proximal side.

For simplification, the parts or elements of one embodiment which are found identically or similarly in another embodiment will be identified using the same numerical references and will not be described again.

FIGS. 12 to 17 illustrate a vertebral osteosynthesis material 1, in particular for the osteosynthesis of two cervical vertebrae, comprising an implant 2 in staple form and an intervertebral cage 3. The implant 2 has two lateral branches 6 designed to be inserted into the plates of the respective vertebrae 100 to be immobilized, and the cage 3 is designed to be inserted between these vertebrae 100, in the discal space previously hollowed out as a result.

Figure 4:
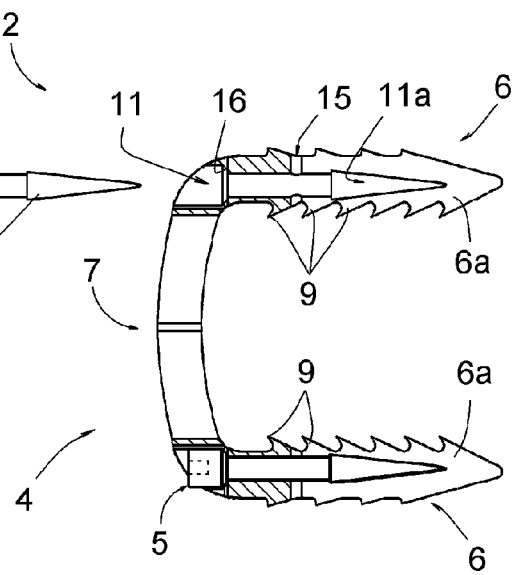
FIG. 4 is a side view of the implant, in longitudinal cross-section, this implant comprising said piece in staple form and two rods, one of which is placed in said piece while the other is not placed in this piece.
Figure 5:
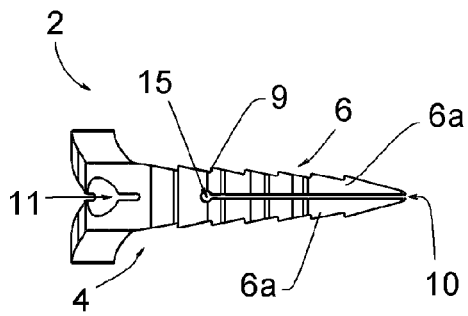
FIG. 5 is a side view of the implant, before placement of said rods.
Figure 6:
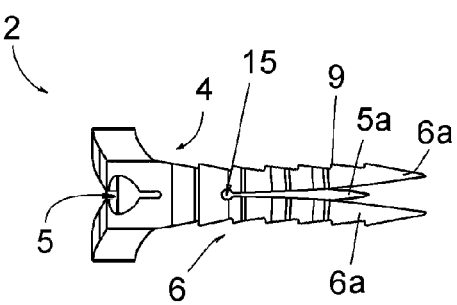
FIG. 6 is a view similar to FIG. 5, after placement of said rods.

In reference to FIGS. 4 to 6, it appears that the implant 2 comprises a piece 4 in staple form and two rods 5. The implant 2 is made in a rigid material having a degree of elastic flexibility, in particular in a biocompatible metal such as titanium or a titanium alloy generally used to produce a bone implant.

As shown by FIGS. 1 to 5, the piece 4 comprises the two parallel lateral branches 6 and a central branch 7 connecting these two lateral branches to each other, these branches 6 and 7 forming a single piece with each other.

Each lateral branch 6 has a substantially square transverse section and ends in a tip at its free end. It has series of teeth and steps 9 protruding from each of its faces, and comprises a slot 10 and a longitudinal internal channel 11.

The slot 10 goes all the way through the branch 6 and is arranged from the free end of this branch 6, in the plane in which the two lateral branches 6 extend. This slot 10 thus defines two distal portions 6a of the branch 6 able to be separated from each other in relation to a longitudinal central axis of the branch, as appears by comparing FIGS. 5 and 6.

On the proximal side, each slot 10 opens into a transverse bore 15 arranged in the lateral branch 6.

The channel 11 is arranged inside the lateral branch 6 and opens at the proximal end thereof, in the connection zone of this lateral branch 6 to the central branch 7. It extends from this zone to between the portions 6a defined by the slot 10.

The channel 11 has a distal portion and a proximal portion, the proximal portion having a diameter larger than the diameter of the distal portion, such that a shoulder 16 is defined between these proximal and distal portions.

The channel 11 also has a slender portion 11a, i.e. in which its transverse section narrows in the distal direction. This portion 11a extends at the level of said portions 6a.

The central branch 7 is diamond-shaped, i.e. comprises two portions 7a bent at their centers, the bends being oriented opposite each other. Like the implant described by French patent application no. 05 04745, these portions 7a can be deformed by the exertion, at their ends, of antagonistic pressures directed toward the outside of these portions 7a, so as to deform these potions 7a in order to reduce the length of the branch 7 and, in so doing, to bring the lateral branches 6 closer to each other.

Each rod 5 is designed to be engaged in the channel 11 of a lateral branch 6 to between the portions 6a of this branch, so as to separate these two portions 6a from each other, as shown by FIG. 6. This rod 5 has a body and a proximal head, this head having a diameter larger than that of this body such that a shoulder 18 is arranged between the head and the body. The proximal head comprises a cavity making it possible to wedge the end of a tool used to impact each rod 6 in a channel 11.

Each rod 5 also has a slender distal end 5a located, when the rod 5 is completely engaged in a corresponding channel 11 (cf. FIG. 4), at the slender portion 11a of the channel 11.

Figure 7:
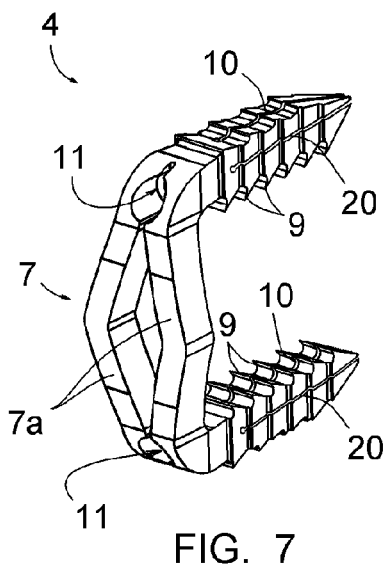
FIG. 7 is a view similar to FIG. 1 of said piece in staple form, according to a second embodiment.
Figure 8:
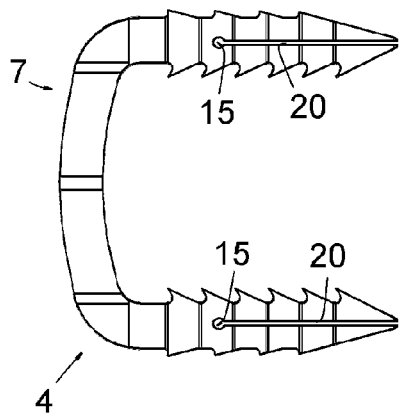
FIGS. 8 and 9 are views of this piece similar to FIG. 2, before and after separation of the mobile portions comprised by this piece.
Figure 9:
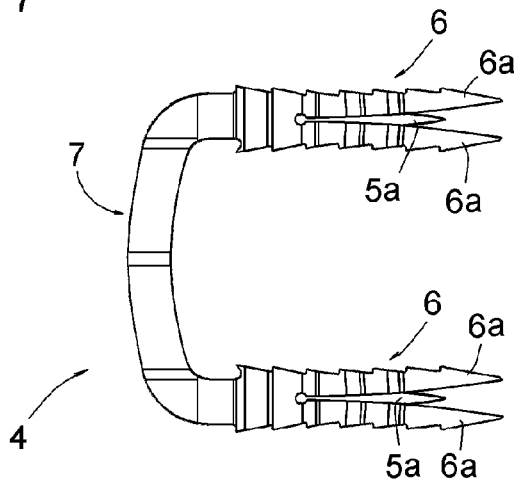

In the embodiment of FIGS. 7 to 9, each branch 6 comprises a slot 20 perpendicular to the slot 10. The four portions 6a defined by these slots 10, 20 separate both as shown in FIG. 9 and as shown in FIG. 6 at the same time.

Of course, at least one branch 6 could comprise only the slot 20.

Figure 10:
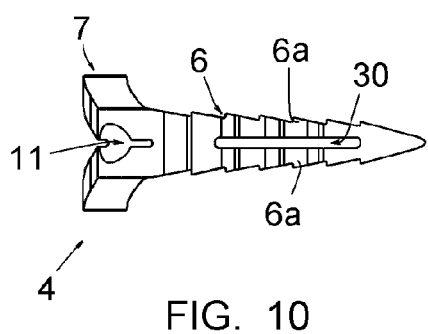
FIG. 10 is a view of said piece similar to FIG. 5 of said piece in staple form, according to a third embodiment.
Figure 11:
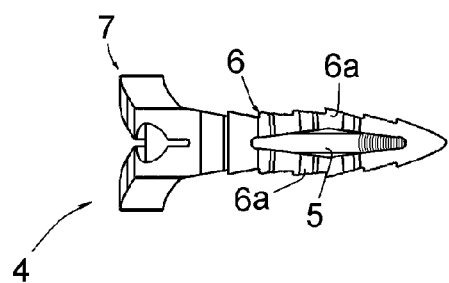
FIG. 11 is a view of this piece similar to FIG. 10, after separation of the mobile portions comprised by this piece.

In the embodiment shown in FIGS. 10 and 11, at least one branch 6 comprises a slot 30 which does not open into its free end. The longitudinal internal channel 11 is then tapped at the free end of the branch 6 and the rod 5 has a distal screw thread which engages with this tapping. The screwing of the rod 5 into this channel 11 makes it possible to achieve the deformation of the portions 6a as visible in FIG. 11.

In practice, as shown in FIGS. 12 to 17, the cage 3 is inserted between the vertebrae 100, then the piece 4 is placed by simultaneous introduction, by impaction, of its two lateral branches 6 into the holes arranged to this end in the vertebral bodies of the respective vertebrae 100. The portions 6a of one lateral branch 6 are then found in the same position as shown in FIG. 5, in which they are close to each other and located in the extension of the rest of the branch 6. The branches 6 then have, at their mobile portions 6a, transverse sections smaller than those of the holes having allowed the introduction of these branches 6 into the vertebral bodies.

Once the lateral branches 6 are implanted in the vertebral bodies, the rods 5 are inserted into the channels 11 so as to bring said mobile portions 6a into the position separated from each other shown in FIG. 16. This separation makes it possible to grant the branches 6, at their mobile portions 6a, sections larger than those of the holes having allowed the introduction of these branches 6 into the vertebral bodies, and therefore to achieve resistant anchoring of the implant 2 to these vertebral bodies. These rods 5 are forcibly engaged inside channels 11, until their shoulders 18 abut against the shoulders 16 of the channels 11, and are held by the lateral branches 6 simply due to the tightening exerted on them by the portions 6a, by elastic return of the material constituting the branches 6.

The bores 15 favor the deformation of this material in order to allow the separation of the portions 6a, and make it possible to avoid any beginning of cracking of this material.

The central branch 7 can then, like the implant known from French patent application no. 05 04745, be shortened by the aforementioned transverse deformations done on the portions 7a, so as to bring the lateral branches 6 closer to each other, and therefore to bring the two vertebrae 100 closer together in order to apply them tightly against the cage 3 previously placed.

As appears from the preceding, the invention provides a vertebral osteosynthesis material having the determining advantage of including an implant 2 able to be anchored with resistance in the vertebral bodies, thereby eliminating the risk of the appearance of play of the vertebrae in relation to this implant 2, or of expulsion of this implant 2 outside these vertebral bodies.

The invention was described above in reference to embodiments provided as examples. It goes without saying that it is not limited to these embodiments and that it extends to all other embodiments covered by the appended claims.

The invention claimed is:

1. Vertebral osteosynthesis material, comprising a graft or an intervertebral piece or cage designed to be inserted between two vertebrae, and an implant in the form of a staple, having two lateral branches designed to be inserted into the plates of the respective vertebrae to be immobilized and a central branch connecting these two lateral branches to each other by forming a single piece with them; each lateral branch has a longitudinal central axis; the central branch can be shortened after implantation so as to allow said lateral branches to come closer to each other and to thus achieve tight application of the vertebrae on the graft or on the intervertebral piece or cage;

wherein:

at least one lateral branch comprises at least one mobile portion, movable between an introduction position, in which this mobile portion is located close to said longitudinal central axis of the lateral branch and in a remainder of the lateral branch, and an anchoring position, in which this mobile portion is moved away from said longitudinal central axis of the lateral branch and protrudes laterally in relation to the remainder of the lateral branch, the lateral branch thus having, in this anchoring position, at said mobile portion, a transverse section greater than that of a hole having allowed introduction of this branch into the vertebral body of the vertebra receiving said lateral branch;

each of the at least one mobile portion is provided with protruding reliefs able to be inserted into the bone of a vertebra, and the implant comprises movement means, allowing the movement of said mobile portion between said introduction and anchoring positions.

2. Material according to claim 1, wherein:

said lateral branch comprises at least one slot which goes all the way through it and an internal channel extending from a zone of this lateral branch connected to said central branch to the portions of this lateral branch defined by the at least one slot, and said movement means comprise a rod designed to be engaged in said internal channel up to between said portions of the lateral branch defined by the at least one slot, so as to separate these portions from each other.

3. Material according to claim 2, wherein the at least one slot is arranged from a respective free end of the lateral branch, such that the at least one slot leads into the respective free end.

4. Material according to claim 2, wherein the at least one slot is arranged such that they do not open into a respective free end of the lateral branch.

5. Material according to claim 2, wherein said lateral branch comprises a single slot.

6. Material according to claim 5, wherein said slot is arranged in a plane in which the two lateral branches of the implant extend, such that the mobile portions defined by said slot are mobile in a plane perpendicular to that in which the two lateral branches of the implant extend.

7. Material according to claim 5, wherein said slot is arranged in a plane perpendicular to a plane in which the two lateral branches of the implant extend.

8. Material according to claim 2, wherein said lateral branch comprises several slots.

9. Material according to claim 2, wherein at least one slot, on a proximal side, opens into a bore arranged in said lateral branch transversely to said longitudinal central axis.

10. Material according to claim 2, wherein said rod constituting the movement means is smooth and dimensioned such that it is engaged forcibly inside said internal channel.

11. Material according to claim 2, wherein said internal channel has a slender shape at said portions defined by the at least one slot, and said rod has a slender distal end.

12. Material according to claim 2, wherein:

said rod has a body and a proximal head with a diameter greater than that of the body, such that a shoulder is defined between this head and this body, and said internal channel has a distal portion and a proximal portion with a diameter greater than a diameter of the distal portion, such that a shoulder is defined between these proximal and distal portions, these respective shoulders making it possible, through their abutment, to define a position of complete introduction of said rod into said lateral branch.

13. Material according to claim 1, wherein each of the two lateral branches comprises at least one mobile portion as previously mentioned and movement means as previously mentioned.

14. Material according to claim 1, wherein said lateral branch comprising said at least one mobile portion has a square or rectangular transverse section, such that it has four flat lateral faces, each of these four flat lateral faces having protruding reliefs able to be inserted into the bone of a vertebra.

15. Surgical method using the material according to claim 1, wherein it comprises the following steps:

in any order, insertion of a graft or an intervertebral piece or cage between two vertebrae and arrangement in the plates of these vertebrae of holes for receiving lateral branches of the implant;

engagement of the lateral branches of the implant in these receiving holes, said at least one mobile portion being in the introduction position;

shortening of said central branch so as to make it possible to bring said lateral branches closer to each other and thereby achieve a tight application of the vertebrae on the graft or the intervertebral piece or cage;

movement of said at least one mobile portion into the anchoring position.

16. Surgical method according to claim 15, wherein it comprises the step of connecting the central branch to said intervertebral piece or cage.

* * * * *